United States Patent [19]

Beauchamp

[11] Patent Number: 4,714,701

[45] Date of Patent: Dec. 22, 1987

[54] ANTIVIRAL COMPOUNDS

[75] Inventor: Lilia M. Beauchamp, Raleigh, N.C.

[73] Assignee: Burroughs Wellcome Co., Research Triangle Park, N.C.

[21] Appl. No.: 859,076

[22] Filed: May 2, 1986

[30] Foreign Application Priority Data

May 2, 1985 [GB] United Kingdom ............. 8511222
May 2, 1985 [GB] United Kingdom ............. 8511224

[51] Int. Cl.$^4$ .................. C07D 473/18; A61K 31/52
[52] U.S. Cl. .................................. 514/258; 544/254; 544/276; 544/277
[58] Field of Search ............... 544/277, 276, 254, 258

[56] References Cited

U.S. PATENT DOCUMENTS 4,027,025 5/1977 Schaeffer ........................ 544/254

FOREIGN PATENT DOCUMENTS 0193454 9/1986 European Pat. Off. .
2130204 5/1984 United Kingdom .

*Primary Examiner*—Nicholas S. Rizzo
*Attorney, Agent, or Firm*—Donald Brown

[57] ABSTRACT

Compounds of formula (I)

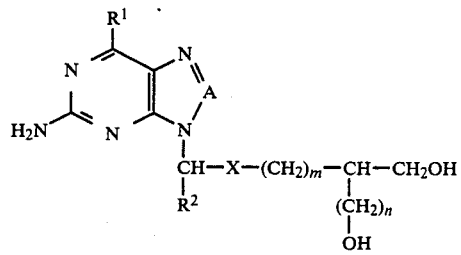

(wherein A represents a

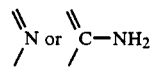

grouping; $R^1$ represents a hydrogen or halogen (e.g. chlorine or bromine) atom or a hydroxy or amino group, $R^2$ represents a hydrogen atom or a $C_{1-4}$ alkyl (e.g. methyl) group, X represents an oxygen or sulphur group and m and n are each 0 or 1 provided that m+n=1) and physiologically acceptable salts and esters thereof, have been found to have potent antiviral activity particularly against herpes infections.

11 Claims, No Drawings

ANTIVIRAL COMPOUNDS

The present invention relates to novel 8-amino-purine derivatives having useful antiviral activity particularly against viruses of the herpes family.

U.K. Pat. No. 1523865 describes a broad class of purine derivatives containing an acyclic side chain in the 9-position. These purine derivatives have been found to have antiviral activity against various classes of DNA viruses particularly against herpes viruses such as herpes simplex. Among these derivatives, 9-(2-hydroxyethoxymethyl)guanine (otherwise known as acyclovir) has been found to have particularly good activity against herpes simlex virus. Other purine derivatives containing an acyclic side chain in the 9-position including for example an analogue of acyclovir containing a 2-hydoxy-1-hydroxymethylethoxymethyl group in the 9-position, described in U.K. Pat. No. 2104070A.

We have now discovered good antiviral activity against certain viruses described below in a class of purine derivatives having a nitrogen-containing group at the 8-position and containing an acyclic side chain in the 9-position.

According to one feature of the present invention we provide compounds of the general formula (I)

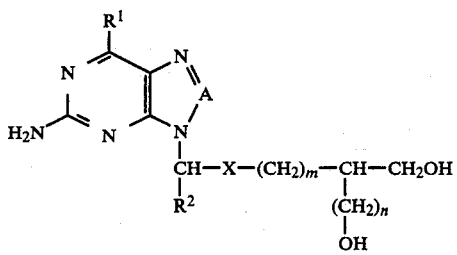

wherein A represents a

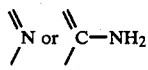

grouping; $R^1$ represents a hydrogen or halogen (e.g. chlorine or bromine) atom or a hydroxy or amino group, $R^2$ represents a hydrogen atom or a $C_{1-4}$ alkyl (e.g. methyl) group, X represents an oxygen or sulphur group and m and n are each 0 or 1 provided that $m+n=1$ and physiologically acceptable salts and salts and esters thereof.

The present invention thus includes the following sub-classes of formula (I) namely formulae (IA) (wherein A represents a $$\underset{/}{\overset{\\}{N}}$$

group) and (IB) (wherein A represents a $$\underset{/}{\overset{\\}{C}}-NH_2$$

group and physiologically acceptable salts and esters thereof.

Salts of the compounds of formula (I) which may be conveniently used in therapy include physiologically acceptable salts of organic acids such as lactic, acetic, malic or p-toluenesulphonic acid as well as physiologically acceptable salts of mineral acids such as hydrochloric or sulphuric acid. Also, when $R^1$ is a hydroxy group, physiologically acceptable salts include the physiologically acceptable alkali metal salts, e.g. the sodium and potassium salts, as well as ammonium including tetralkylammonium salts.

Esters of the compounds of formula (I) which may be conveniently used in therapy include those containing a formyloxy or $C_{1-16}$ (for example $C_{1-6}$)alkanoyloxy (e.g. acetoxy or propionyloxy), optionally substituted aralkanoyloxy (e.g. phenyl-$C_{1-4}$alkanoyloxy such as phenylacetoxy) or optionally substituted aroyloxy (e.g. benzoyloxy or naphthoyloxy) or phosphate ester grouping at one or both of the terminal positions of the 9-side chain of the compounds of formula (I). The above-mentioned aralkanoyloxy and aroyloxy ester groups may be substituted, for example by one or more halogen (e.g. chlorine or bromine) atoms or amino, nitrile or sulphamido groups, the aryl moiety of the grouping advantageously containing 6 to 10 carbon atoms.

According to a further feature of the present invention we provide a compound of formula (I) and physiologically acceptable salts and esters thereof for use in therapy prticularly for use in the treatment or prophylaxis of a viral disease in an animal, e.g. a mammal such as man.

The present invention also provides a method for the treatment or prophylaxis of a viral disease in an animal, e.g. a mammal such as man which comprises administering to the animal an effective antiviral amount of the compound of formula (I) or a physiologically acceptable salt or ester thereof.

The present invention further provides the use of a compound of formula I or a physiologically acceptable salt or ester thereof in the manufacture of a medicament for the treatment or prophylaxis of a viral disease.

The compounds of formula (I) and their physiologically acceptable salts and esters have a particularly effective activity against DNA viruses particularly those of the herpes family including herpes simplex, varicella zoster, cytomegalovirus (CMV) and Epstein-Barr (EBV) virus, as well as hepatitis B. Those compounds of formula (IA) have been found to have particularly high activity against CMV and EBV infections, 5-amino-3,6-d, hydro-3-[(2-hydroxy-1-hydroxymethylethoxy)methyl]-7H-1,2,3-triazolo[4,5-d]pyrimidin-7-one having especially potent activity.

Those compounds of formula (IB) have been found to have particularly good activity against herpes simplex, 8-amino-9-[2-hydroxy-1-(hydroxymethyl)ethoxymethyl]guanine being especially preferred for its particularly high activity against herpes simplex.

The compounds of formula (I) and the physiologically acceptable salts and esters thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with for example the condition of the recipient.

According to yet another feature of the present invention we provide a compound of formula (I) wherein $R^1$ is halogen for use as a chemical intermediate useful in the preparation of compounds of formula (I) wherein $R^1$ is hydrogen, hydroxy or amino.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilites and indications, a suitable, effective dose will be in the range 0.1 to 250 mg per kilogram bodyweight of recipient per day, preferably in the range 1 to 100 mg per kilogram bodyweight per day and most preferably in the range 5 to 20 mg per kilogram bodyweight per day; an optimum dose is about 10 mg per kilogram bodyweight per day. (Unless otherwise indicated all weights of active ingredient are calculated as the parent compound of formula (I): for salts and esters thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/fat make up the so-called emulsifying ointment base which forms the oily dispersed phase of the cream formulations.

Emulgents and emulsion stabilisers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The compounds of formula (I) and its their physiologically acceptable salts and esters may be prepared in conventional manner by analogous processes for preparing compounds of similar structure, such as those methods described in U.K. Pat. Nos. 1523865 and 2104070.

According to a further feature of the present invention there is provided a process for preparing compounds of formula (I) and physiologically acceptable salts and esters thereof, characterised in that:

(a) a compound of formula

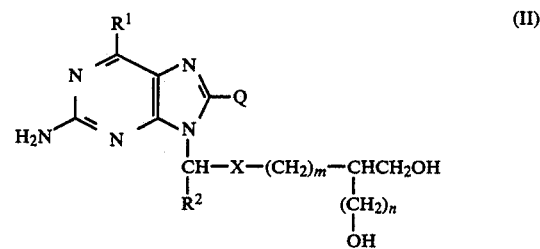

(wherein Q represents a leaving group and $R^1$, $R^2$, m, n and X are as defined above) is reacted with an aminating agent serving to replace the leaving group Q by an amino group) to produce a compound of formula (IB);.

(b) a compound of formula (III)

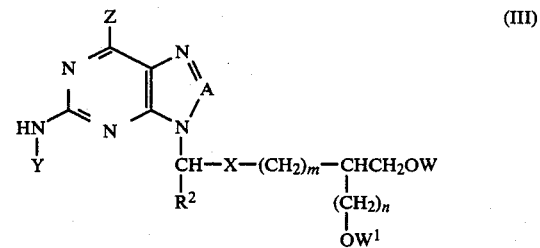

(wherein X, $R^2$, m and n are as defined above and W and $W^1$ each represent a hydrogen atom or blocking group, Y is a hydrogen atom or a blocking group and Z is a hydrogen atom or a group of formula —OY or —NHY wherein Y is as defined above providing that at least one of W, $W^1$ and Y represent a blocking group), is deblocked to form a compound of formula (I) or a salt or ester thereof;

(c) a compound of formula (IV)

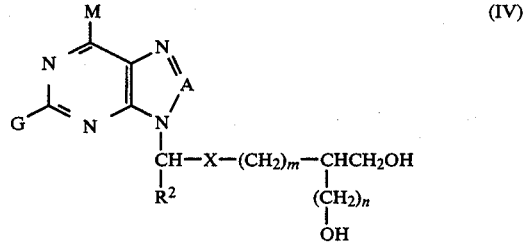

(wherein X, $R^2$, m and n are as defined above and M represents a hydrogen atom or a hydroxy or amino group or an atom or group convertible into such atom or group and G represents an atom or group convertible into an amino group or (when M is other than a hydrogen atom or a hydroxy or amino group) (G may alternatively represent an amino group) or a salt or ester thereof, is converted into a compound of formula (I) or a salt or ester thereof;

(d) a compound of formula (V)

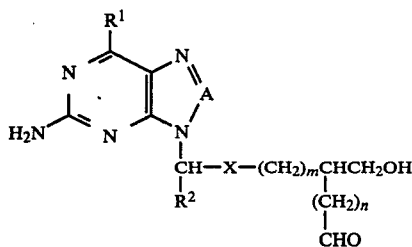

(V)

(wherein $R^1$, $R^2$, m, n and X are as defined above) or a salt or ester thereof is reduced;

(e) a compound of formula (VI)

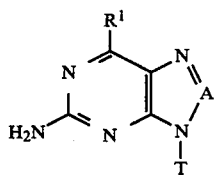

(VI)

(wherein $R^1$ is as defined above and T is a leaving group or atom) is reacted with a compound of formula

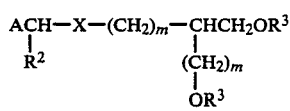

(VII)

(wherein X, $R^2$, m and n are as defined above, $R^3$ is a blocking group and A is a leaving group or atom); and optionally effecting one or more of the following conversions, in any desired sequence:

(i) where the resulting product is a base, converting the said base into a physiologically acceptable acid addition salt thereof;

(ii) where the resulting product is an acid additon salt, converting the said salt into the parent base;

(iii) where the resulting product is a compound of formula (I) or a salt thereof converting the said compound or salt thereof into a physiologically acceptable ester of the said compound or salt; and/or (iv) where the resulting product is an ester of a compound of formula (I) converting the said ester into the parent compound of formula (I), a physiologically acceptable salt thereof or a different physiologically acceptable ester thereof.

In method (a) the leaving group is conveniently a halogen atom, e.g. a bromine atom and the aminating agent is conveniently hydrazine or ammonia. The starting material of formula (II) may be prepared in conventional manner from the corresponding 8-unsubstituted compound, e.g. by bromination in the case of the above-mentioned 8-bromo starting material.

In methods (b) and (e) the blocking groups may be selected, as appropriate, for example from acyl groups such as $C_{1-4}$alkanoyl groups e.g. acetyl or pivaloyl, or aroyl groups, e.g. benzoyl; arylmethyl groups e.g. benzyl; or tri-$C_{1-4}$alkylsilyl e.g. trimethylsilyl. Arylmethyl blocking groups may be removed for example by hydrogenolysis, e.g. by hydrogenation in the presence of Raney nickel or palladium catalyst or by the use of sodium in liquid ammonia. Acyl blocking groups may be removed for example by hydrolysis using for example an amine such as methylamine or triethylamine, advantageously in an aqueous medium. Trialkylsilyl blocking groups may be removed for example by solvolysis e.g. with alcoholic or aqueous ammonia, or by alcoholysis.

Conversion of a compound of formula (IV) into a compound of formula (I), by method (c), can be achieved by various conventional means. For example G may represent an azide group which can be reduced to an amino group by catalytic hydrogenation using a suitable catalyst such as palladium. Alternatively, G may represent a halogen atom or an alkylthio or alkylsulphonyl group which can be converted to an amino group by aminolysis using for example ammonia. M may represent a halogen, e.g. chlorine, atom or a mercapto or thio (S=) group which can be converted into a hydrogen atom in conventional manner. In the case where M represents a thio group, this conversion may be effected using a compound of formula (IV) in which any amino or hydroxyl groups are optionally blocked by acyl groups, the conversion being effected using a Raney nickel catalyst, e.g in a basic medium which additionally removes the amino and/or hydroxy blocking groups in accordance with process (b).

These processes together with other conventional processes are described in Fused Pyrimidines, Part II, Purines Ed. by D. J. Brown (1971), Wiley-Interscience.

Reduction of a compound of formula (V) in process (d) may be achieved for example by reaction with an appropriate aldehyde reducing agent such as sodium borohydride, sodium cyanoborohydride, tetraethylammonium borohydride or pyridine/diborane/tetrahydrofuran/trifluoroacetic acid.

In process (e), the group T in formula (VI) may for example represent a hydrogen atom; an acyl group, e.g. a $C_{1-4}$alkanoyl group such as an acetyl group or an aroyl group such as a benzoyl group; or a tri-$C_{1-4}$alkylsilyl group such as a trimethylsilyl group. The group A in formula (VII) may for example represent a halogen atom (e.g. chlorine) or an acyloxy group wherein the acyl moiety may be for example a $C_{1-4}$alkanoyl group such as acetyl, or an aroyl group such as benzoyl. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (VI) and (VII) in the presence of a catalytic amount of a strong acid, e.g. sulphuric acid.

The starting materials employed in the processes described above may be prepared in conventional manner, e.g. in accordance with the processes described in the above-mentioned U.K. Pat. Nos. 1523865 and 2104070.

The following Examples illustrate the present invention.

EXAMPLE 1

8-Amino-9-[(2-hydroxy-1-hydroxymethylethoxy)methyl]guanine (a)
8-Bromo-9-[(2-hydroxy-1-Hydroxymethylethoxy)methyl]guanine To a suspension of 2.44 g (9.57 mM) of 9-[(2-hydroxy-1-hydroxymethylethoxy)methyl]guanine in 220 ml of water was added 200 ml of bromine water, dropwise at room temperature with stirring. (the bromine water was prepared by stirring 20 ml of bromine with 750 ml of water and decanting off the supernatant after 10 minutes). After the addition of 150 ml of the bromine solution a precipitate began to form. The mixture was stirred at room temperature for 2 hours longer. The TLC (silica gel in 30% MeOH-CH$_2$Cl$_2$) showed complete conversion of the starting material.

The mixture was chilled in a refrigerator for three hours, filtered, washing with water and dried to give 3.0 g of the title compound. The 1H NMR spectrum was satisfactory. A 400 mg portion was recrystallised from boiling water to give 316 mg of analytically pure product which gave a satisfactory elemental analysis (CHNBr).

HPLC assay on C$^{18}$ reverse phase column in 30% MeOH-H$_2$O showed the initial precipitate was 99% pure. Yield 74% based on recovery of analytical pure anhydrous material.

(b)
8-Amino-9-[(2-hydroxy-1-hydroxymethylethoxy)methyl]guanine

A mixture of 0.87 g (2.6 mM) of 8-bromo-9-[(2-hydroxy-1-hydroxymethylethoxy)methyl]-guanine and 25 ml of water was heated on a steam bath until solution occurred. To the solution was added 0.6 ml of 95% hydrazine and the reaction solution heated on a steam bath for 18 hours. The clear solution was evaporated in vacuo and the residue triturated with water to give 0.71 g of white powder. Assay by HPLC (C$^{18}$ reverse phase in 30% MeOH-H$_2$O) showed the precipitate was largely unreacted starting material and the mother liquors contain starting material and product. The two components were recombined and refluxed with 1 ml more of 95% hydrazine for 18 hours.

A tea-coloured precipitate was filtered off from the cooled reaction mixture to give 0.6 g of a beige solid. The latter was recrystallised from water to yield 0.38 g of a blue-gray pecipitate. The mother liquors turned dark blue on standing overnight.

Assay by HPLC on the recrystallised gray solid showed a minor impurity was present. The material was recrystallised from water and charcoal to yield the title compound as 210 mg of charcoal-gray crystals (30%) mp >250° C. The elemental analysis and 1H-NMR spectrum were consistent with the desired structure.

EXAMPLE 2

5-Amino-3,6-dihydro-3-[(2-hydroxy-1-hydroxymethylethoxy)methyl]-7H-1,2,3-triazolo[4,5-d]pyrimidin-7-one A mixture of 10 g (65.8 mM) of 8-azaguanine, 7.2 g (NH$_4$)$_2$SO$_4$ (54.5 mM) and 500 ml of hexamethyldisilazane was refluxed for 18 hours. The solution was evaporated in vacuo to a light yellow oil and dissolved in about 200 ml dry toluene. To this solution was added 29 g (75 mM) of 2-O-(bromomethyl)-1,3-bis(O-benzoyl)-glycerol and the solution was refluxed for 18 hours. The resulting reaction mixture at pH 1 was neutralised dropwise with triethylamine, then evaporated in vacuo to near dryness. 95% Ethanol was added to this semi-solid mixture causing the precipitation of 23 g (49.5 mM) of finely divided, nearly pure alkylated azaguanine which was collected by filtration. 2.0 g of the alkylated azaguanine were debenzoylated by stirring for 20 minutes at room temperature in excess 40% aqueous methylamine. The reaction mixture was evaporated to half volume then extracted twice with benzene to remove the N-methyl benzamide. The H$_2$O layer was evaporated to near dryness followed by purification of the product by flash chromatography on silica gel eluting with 3:1 CH$_2$Cl$_2$:MeOH which yielded 0.8 g (3.0 mM) of the title compound as an analytically pure, white product, m.pt. 233°–234° (overall yield 56%).

EXAMPLE 3

5-Amino-3-[(2,3-dihydroxypropoxy)methyl]-3,6-dihydro-7H-1,2,3-triazolo[4,5-d]-7-one (a) 1,5-diacetyl-8-azaguanine A mixture of 5.0 g (0.33M) of 8-azaguanine in 450 mL of acetic anhydride was refluxed for 2 hours, then stirred at room temperature for 18 hours.

The solids were filtered off to give the title compound. This had a satisfactory elemental analysis.

(b) A mixture of 2.6 g (0.011M) of 1,5-diacetyl-8-azaguanine, 55 mg (0.5 mM) of ethanesulfonic acid and 5.5 g (0.022M) of acetoxymethyl 2,3-diacetoxy-1-propyl ether* was heated at 155° C. under water aspirator pressure for 1 hour. The reaction mixture was dissolved in CH$_2$Cl$_2$ and absorbed on a column of silica gel. Elution with 2.8 liters of 2% methanol in CH$_2$Cl$_2$ yielded, after evaporation of the second 1.4 liters of eluant, the product. The material was purified twice more by column chromatography, eluting the desired compound with 1:2 ethyl acetate/ether each time. The product was dissolved in 30% aqueous methylamine and stirred at room temperature for 2 hours. The solvent was removed by flash evaporation and the residue recrystalized from methanol to give the title compound. The elemental anlaysis, UV and $^1$H NMR were consistent with the desired structure.

*The synthesis of this compound is described in European Pat. No. 0074306.

EXAMPLE 4

2-[(2,6-Diamino-8-bromo-9H-purin-9-yl)methoxy]-1,3-propanediol

To a solution of 2.50 g (9.83 mM) of 2,6-diamino-9-(2-hydroxy-1-(hydroxymethyl)ethoxymethyl)-9H-purine in 135 ml of water was added dropwise 60 ml of bromine water over a period of 1.5 hours. The solution was stirred at room temperature for 1.25 hours then placed on a rotary evaporator for 30 minutes to remove excess bromine. The solutio was chilled and the pH adjusted to 8 with concentrated ammonium hydroxide, then stored at 6° C. for two days.

A precipitate was filtered from the cooled reaction mixture to yield the title compound as a faint yellow powder; mp 225°–228° C. (gradually darkens before melting).

The elemental analysis, UV and $^1$H UMR spectra were consistent with the desired structure.

EXAMPLE 5

2-[(2,6,8-Triamino-9H-purin-9-yl)methoxy]-1,3 propanediol

A mixture of 1.153 g (3.46 mM) of 2-[(2,6-diamino-8-bromo-9H-purin-9-yl)methoxy]-1,3-propanediol and 300 ml of a saturated solution of ammonia in methanol was heated at 125° C. in a Parr bomb for 18 hours. The reaction mixture was purified by flash chromatography on silica gel eluting with a methanol dichloromethane gradient (10→40%) to give a light brown solid. This solid was recrystallized from acetonitrile/methanol to yield the title compound as a light brown powder, mp 206°–208° C.

The elemental analysis (UV and $^1$H NMR spectra) were consistent with the desired structure.

The following Examples illustrate pharmaceutical formulations according to the invention in which the active compound is a compound of formula (I) e.g. the compound described in Example 1.

EXAMPLE 6

Tablet

| | |
|---|---|
| Active compound | 200 mg |
| Lactose | 235 mg |
| Starch | 50 mg |
| Polyvinylpyrrolidone | 50 mg |
| Magnesium stearate | 5 mg |
| | 500 mg |

Mix the active compound with the lactose and starch and wet granulate with a solution of the polyvinylpyrrolidone. Dry, sift, blend the granules with magnesium stearate and compress.

EXAMPLE 7

Capsule

| | |
|---|---|
| Active compound | 200 mg |
| Lactose | 184 mg |
| Sodium starch glycollate | 8 mg |
| Polyvinylpyrrolidone | 6 mg |
| Magnesium stearate | 2 mg |

Mix the active compound with the lactose and sodium starch glycollate and wet granulate with a solution of the polyvinylpyrrolidone. Dry, sift, blend the granules with the magnesium stearate and fill into hard gelatin capsules.

EXAMPLE 8

Cream

| | |
|---|---|
| Active compound | 5.00 g |
| Glycerol | 2.00 g |
| Cetostearyl alcohol | 6.75 g |
| Sodium lauryl sulphate | 0.75 g |
| White soft paraffin | 12.50 g |
| Liquid paraffin | 5.00 g |
| Chlorocresol | 0.10 g |
| Purified water to | 100.00 g |

Dissolve the active compound in a mixture of purified water and glycerol and heat to 70° C. Heat the remaining ingredients together at 70° C. Add the two parts together and emulsify. Cool and fill into containers.

EXAMPLE 9

Intravenous Injections (A)

Active compound: 200 mg
Sodium hydroxide solution: q.s. to pH 7.0 to 7.5
Water for injections: to 5.0 ml Dissolve the active compound in part of the water for injections. Adjust the pH with the sodium hydroxide solution and make up to volume with additional water for injections. Under aseptic conditions, sterilise the solution by filtration, fill into sterile ampoules and seal the ampoules.

(B)

Active compound: 100 mg
Sodium hydroxide solution: q.s. to pH 7.0 to 7.5
Mannitol: 125 mg
Water for injections: to 2.5 ml Dissolve the active compound and mannitol in part of the water for injections. Adjust the pH with the sodium hydroxide solution and make up to volume with additional water for injections. Under aseptic conditions, sterilise the solution by filtration, fill into sterile vials and remove the water by freeze-drying. Seal the vials under an atmosphere of nitrogen and close with a sterile stopper and aluminium collar.

ANTIVIRAL ACTIVITY (a) Anti-HSV Activity

The inhibiting effect of the compounds of Example 1 and 2 against herpes simplex virus were determined by the plaque reduction assay. The $IC_{50}$ of the compounds we found to be 0.5 μM and 27.4 μM respectively.

(b) Anti-CMV Activity

The inhibitory effect of the compound of Example 2 against CMV was determined by a ten day plaque reduction assay in human foreskin fibroblast cells infected with the Kerr strain of CMV.

The $IC_{50}$ of the compound was found to be 4.7, 6.2 and 17.9 μM in a series of assays.

(c) Anti-EBV Activity

The inhibitory effect of the compound of Example 2 against EBV was determined by the method described by Nonogama 1. Pagano, 1971, Nature: New Biology, Vol. 233, 103–104.

The $IC_{50}$ of the compound was found to be 1–10 μm.

TOXICITY

The toxicity of the compound of Example 2 was determined by administering the compound to dogs at a dosage of 60 mg/kg/day, by the intravenous route. No toxic effects were noted.

I claim:

1. A compound of formula (I)

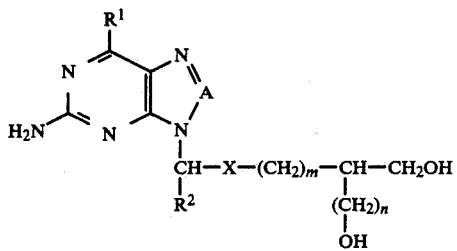 (I)

wherein A is a N; $R^1$ is a hydrogen, cl, Br, hydroxy or amino, $R^2$ is hydrogen or $C_{1-4}$ alkyl, X is oxygen or sulphur and m and n are each 0 or 1 provided that $m+n=1$; or a physiologically acceptable salt or ester thereof.

2. A compound of formula (I) as claimed in claim 1 wherein A is

grouping and $R^1$, $R^2$, X, m and n are as defined in claim 1, and physiologically acceptable salts and esters thereof.

3. A compound according to claim 1 wherein $R^1$ is a halogen atom.

4. A method for the treatment or prophylaxis of a viral infection in an animal comprising administering to the animal an effective antiviral amount of a compound as claimed in claim 1.

5. A method according to claim 4 wherein the said infection is a DNA virus infection.

6. A method according to claim 4 wherein the said infection is a herpes simplex, varicella zoster, CMV, EBV and hepatitis B infections.

7. 5-amino-3,6-dihydro-3-[(2-hydroxy-1-hydroxymethylethoxy)methyl]-7H-1,2,3-triazolo[4,5-d]pyrimidine-7-one.

8. A pharmacologically acceptable salt of the compound of claim 7.

9. 5-amino-3-[(2,3-dihydroxypropoxy)methyl]-3,6-dihydro-7H-1,2,3-triazalo[4,5-d]-7-one.

10. A pharmacologically acceptable salt of the compound of claim 9.

11. A pharmaceutical composition for use as an antiviral comprising the compound salt or ester of claim 1 present in an amount effective as an antiviral.

* * * * *

UNITED STATES PATENT AND TRADEMARK OFFICE
CERTIFICATE OF CORRECTION

PATENT NO. : 4,714,701
DATED : December 22, 1987
INVENTOR(S) : Lilia M. Beauchamp It is certified that error appears in the above—identified patent and that said Letters Patent is hereby corrected as shown below:

Col. 13, line 14 (claim 1), after "wherein A is", cancel "a."

Col. 13, line 14 (claim 1), after "hydrogen,", cancel "cl," and insert --Cl,--.

Col. 14, line 14 (claim 6), after "hepatitis B", cancel "infections" and insert --infection--.

Col. 14, line 21 (claim 9), cancel "dihydro-7H-1,2,3-triazalo[4,5-d]-7-one" and insert --dihydro-7$\underline{H}$-1,2,3-triazolo[4,5-d]pyrimidine-7-one--.

Signed and Sealed this

Fourteenth Day of February, 1989

Attest:

DONALD J. QUIGG

Attesting Officer

Commissioner of Patents and Trademarks